US008410327B2

(12) United States Patent
Tschirschwitz et al.

(10) Patent No.: US 8,410,327 B2
(45) Date of Patent: Apr. 2, 2013

(54) PROCESS FOR ISOMERIZING A SATURATED, BRANCHED AND CYCLIC HYDROCARBON

(75) Inventors: Steffen Tschirschwitz, Mannheim (DE); Stephan Deuerlein, Ludwigshafen (DE); Jochen Bürkle, Mannheim (DE); Markus Schmitt, Heidelberg (DE); Michael Schreiber, Mannheim (DE); Steffen Oehlenschläger, Antwerpen (BE)

(73) Assignee: BASF SE, Ludwigshafen (DE)

( * ) Notice: Subject to any disclaimer, the term of this patent is extended or adjusted under 35 U.S.C. 154(b) by 19 days.

(21) Appl. No.: 12/961,281

(22) Filed: Dec. 6, 2010

(65) Prior Publication Data
US 2011/0137097 A1 Jun. 9, 2011

(30) Foreign Application Priority Data

Dec. 7, 2009 (EP) .................................... 09178208

(51) Int. Cl.
C07C 2/42 (2006.01)

(52) U.S. Cl. .................... 585/371; 585/372; 585/374

(58) Field of Classification Search .................. None
See application file for complete search history.

(56) References Cited

U.S. PATENT DOCUMENTS

| 2,493,567 | A  | 1/1950 | Birch et al.    |
|-----------|----|--------|-----------------|
| 3,233,001 | A  | 2/1966 | Maryfield et al.|
| 5,202,519 | A  | 4/1993 | Khare           |
| 7,351,339 | B2 | 4/2008 | Maase et al.    |
| 7,767,852 | B2 | 8/2010 | Volland et al.  |
| 2003/0109767 | A1 | 6/2003 | Vasina et al. |
| 2003/0181780 | A1 | 9/2003 | Herbst et al. |
| 2008/0083606 | A1 | 4/2008 | Volland et al. |

FOREIGN PATENT DOCUMENTS

| DE | 10202838 A1 | 8/2003 |
| EP | 1 310 472 A1 | 5/2003 |
| EP | 1 346 768 A2 | 9/2003 |
| EP | 1403236 A1 | 3/2004 |

OTHER PUBLICATIONS

U.S. Appl. No. 12/961,308, filed Dec. 6, 2010, Tschirschwitz et al.
International Search Report—PCT/EP2010/068958—Dec. 6, 2010-Nov. 29, 2011.
U.S. Appl. No. 12/961,308, filed Cec. 6. 2010, Tschirschwitz et al.
Ksenofontov, V.A. et al., "Isomerization of cyclic hydrocarbons mediated by an AICl3-based ionic liquid as catalyst," React. Kinet. Catal. Lett. 2003, vol. 80, No. 2, pp. 329-335.
Ono, Y., et al., "The synergism of AlCl3—CuCl2 mixtures int he low-temperature conversion of pentane," Journal of Catalysis 1979, vol. 56, pp. 47-51.
Ono, Y., et al., "Isomerization of Pentane with $AlCl_3$—$CuSO_4$ mixtures," Journal of Catalysis 1980, vol. 64, pp. 13-17.
Ono, Y., et al., "Highly selective isomerization of Pentane with $AlBr_3$-metal sulfate mixtures," Chemistry Letters 1978, pp. 1061-1064.

Primary Examiner — Tam M Nguyen
(74) Attorney, Agent, or Firm — Novak Druce Connolly Bove + Quigg LLP

(57) ABSTRACT

A process for isomerizing a saturated, branched and cyclic hydrocarbon, in which a tertiary carbon atom of the hydrocarbon is converted to a secondary carbon atom in the course of isomerization, by performing the isomerization in the presence of a superacidic ionic liquid comprising an organic cation and an inorganic anion, where the anion is a superacidic aluminum trichloride-Lewis base adduct, and of a copper(II) compound.

17 Claims, No Drawings

PROCESS FOR ISOMERIZING A SATURATED, BRANCHED AND CYCLIC HYDROCARBON

CROSS-REFERENCE TO RELATED APPLICATIONS

This application claims benefit of European application 09178208.6, filed Dec. 7, 2009, the contents of which are incorporated herein by reference in its entirety.

FIELD OF THE INVENTION

The invention relates to a process for isomerizing a saturated, branched and cyclic hydrocarbon, in which a tertiary carbon atom of the hydrocarbon is converted to a secondary carbon atom in the course of isomerization.

BACKGROUND

The isomerization of saturated hydrocarbons (paraffins) to the corresponding branched isomers is an important process, for example, for increasing the research octane number (RON) of gasoline, in order to improve the combustion properties thereof.

Branched cyclic hydrocarbons can isomerize with ring enlargement to less branched cyclic hydrocarbons; one example is the rearrangement of methylcyclopentane (MCP) to cyclohexane. These reactions are catalyzed by strong Lewis acids or strong Brønsted acids.

The isomerization of saturated hydrocarbons with solid aluminum chloride has been known for some time. A frequently used accelerating additive is HCl (e.g. U.S. Pat. No. 2,493,567, U.S. Pat. No. 3,233,001, U.S. Pat. No. 5,202,519). Problems in these processes are the long-term stability of solid aluminum chloride and the removal thereof.

US 2003/0109767 A1 (Vasina et al.) reports that ionic liquids consisting of a nitrogen-containing heterocyclic or aliphatic cation and an anion which derives from a metal halide can be utilized for isomerization of paraffins in the direction of more highly branched paraffins at relatively low temperatures.

Cyclic hydrocarbons with a tertiary carbon atom as additives, such as methylcyclohexane and dimethylcyclopentane, according to EP 1 403 236 A1 (Haldor Topsoe A/S), increase the selectivity with regard to the formation of more highly branched hydrocarbons from less branched or unbranched hydrocarbons.

Ionic liquids consisting of n-butylpyridinium chloride and aluminum chloride can be utilized in order to isomerize methylcyclopentane and cyclohexane: V. A. Ksenofontov, T. V. Vasina, Y. E. Zubarev, L. M. Kustov, React. Kinet. Catal. Lett. 2003, Vol. 80 (2), pages 329-335.

The utilization of combinations of aluminum halides and copper(II) chloride or copper(II) sulfate, in each case in a ratio of 1:1, for the isomerization of pentane is reported by Ono et al. in Chem. Lett. 1978, 1061-64; J. Catal. 1979, 56, 47-51; and J. Catal. 1980, 64, 13-17.

The isomerization of paraffins with aluminum chloride and copper(II) chloride in molar ratios of 2:1 to 3:1 is described in U.S. Pat. No. 5,202,519 A (Phillips Petroleum Comp.), wherein the selectivity with regard to the isomerization is lower than the selectivity with regard to disproportionation.

US 2003/0181780 A1 (Herbst et al.) reports the isomerization of paraffins to more highly branched hydrocarbons with ionic liquids which comprise aluminum halide and additionally metal halides, for example copper(II) chloride, iron(III) chloride and molybdenum(V) chloride.

BRIEF SUMMARY

It was an object of the present invention to provide, overcoming the disadvantages of the prior art, an improved, economically viable process for isomerizing a saturated, branched and cyclic hydrocarbon.

The preparation process should additionally be particularly simple and economically viable, and should provide the process product (a saturated cyclic hydrocarbon with the same empirical formula and lower degree of branching) in high yields, more particularly in high space-time yields (STY), and selectivities.

Accordingly, a process has been found for isomerizing a saturated, branched and cyclic hydrocarbon, in which a tertiary carbon atom of the hydrocarbon is converted to a secondary carbon atom in the course of isomerization, which comprises performing the isomerization in the presence of a superacidic ionic liquid comprising an organic cation and an inorganic anion, where the anion is a superacidic aluminum trichloride-Lewis base adduct, and of a copper(II) compound.

DETAILED DESCRIPTION OF THE PREFERRED EMBODIMENTS

It has been recognized in accordance with the invention that the isomerization of a saturated, branched and cyclic hydrocarbon can be greatly accelerated and the selectivity increased when the isomerization is performed in the presence of a superacidic ionic liquid comprising aluminum chloride and in the presence of a copper(II) compound as a catalyst.

The process according to the invention is therefore superior to conventional processes, one reason being that the reaction equilibria are attained significantly more rapidly.

The copper(II) compound is preferably a copper(II) salt.

Preferred copper(II) compounds are $CuCl_2$, $CuO$, $CuSO_4$, $CuI_2$, $CuBr_2$, $Cu(OH)Cl$, $Cu(HSO_4)_2$, $Cu(NO_3)_2$.

The copper(II) compound is more preferably $CuCl_2$, $CuO$ or $CuSO_4$.

Particular preference is given to performing the isomerization process according to the invention in the presence of a copper(II) compound in the absence of a further compound of another metal, especially of a further halide of another metal, the metal being particularly a transition group metal.

The isomerization is preferably performed in the presence of 0.1 to 3% by weight, especially >0.1 to 2% by weight, very particularly 0.5 to 1.5% by weight, of the copper(II) compound, based in each case on the superacidic ionic liquid used.

The hydrocarbon to be isomerized is preferably a saturated, branched and cyclic $C_{4-18}$ hydrocarbon, particularly a saturated, branched and cyclic $C_{5-10}$ hydrocarbon, very particularly a saturated, branched and cyclic $C_{5-8}$ hydrocarbon.

The hydrocarbon to be isomerized is more preferably methylcyclopentane (MCP), which is isomerized to the product cyclohexane (CH), and/or 1,2-dimethylcyclopentane, 1,3-dimethylcyclopentane and/or 1,1-dimethylcyclopentane, which are isomerized to the product methylcyclohexane (MCH).

The isomerization process according to the invention converts a tertiary carbon atom of the hydrocarbon to a secondary carbon atom. The isomerization thus affords a less branched saturated hydrocarbon as the product.

A particular example thereof is the isomerization of methylcyclopentane (MCP) to cyclohexane (CH).

The hydrocarbon to be isomerized is preferably used in a concentration in the range from 1 to 90% by weight, particularly from 5 to 20% by weight, based in each case on the ionic liquid.

The isomerization is preferably performed at a temperature in the range from −20 to 150° C., particularly 40 to 100° C.

The isomerization is preferably performed at an absolute pressure in the range from 1 to 10 bar, particularly 1 to 6 bar.

Ionic liquids in the context of the present invention are preferably (A) salts of the general formula (I)

$$[A]_n^+[Y]^{n-} \quad (I)$$

in which n is 1, 2, 3 or 4, $[A]^+$ is a quaternary ammonium cation, an oxonium cation, a sulfonium cation or a phosphonium cation, and $[Y]^{n-}$ is a mono-, di-, tri- or tetravalent anion;

(B) mixed salts of the general formulae (II)

$$[A^1]^+[A^2]^+[Y]^{n-} \quad \text{(IIa) where } n=2;$$

$$[A^1]^+[A^2]^+[A^3]^+[Y]^{n-} \quad \text{(IIb) where } n=3; \text{ or}$$

$$[A^1]^+[A^2]^+[A^3]^+[A^4]^+[Y]^{n-} \quad \text{(IIc) where } n=4$$

where $[A^1]^+$, $[A^2]^+$, $[A^3]^+$ and $[A^4]^+$ are each independently selected from the groups specified for $[A]^+$, and $[Y]^{n-}$ is as defined under (A); or (C) mixed salts of the general formulae (III)

$$[A^1]^+[A^2]^+[A^3]^+[M^1]^+[Y]^{n-} \quad \text{(IIIa) where } n=4;$$

$$[A^1]^+[A^2]^+[M^1]^+[M^2]^+[Y]^{n-} \quad \text{(IIIb) where } n=4;$$

$$[A^1]^+[M^1]^+[M^2]^+[M^3]^+[Y]^{n-} \quad \text{(IIIc) where } n=4;$$

$$[A^1]^+[A^2]^+[M^1]^+[Y]^{n-} \quad \text{(IIId) where } n=3;$$

$$[A^1]^+[M^1]^+[M^2]^+[Y]^{n-} \quad \text{(IIIe) where } n=3;$$

$$[A^1]^+[M^1]^+[Y]^{n-} \quad \text{(IIIf) where } n=2;$$

$$[A^1]^+[A^2]^+[M^4]^{2+}[Y]^{n-} \quad \text{(IIIg) where } n=4;$$

$$[A^1]^+[M^1]^+[M^4]^{2\circ}[Y]^{n-} \quad \text{(IIIh) where } n=4;$$

$$[A^1]^+[M^5]^{3+}[Y]^{n-} \quad \text{(IIIi) where } n=4; \text{ or}$$

$$[A^1]^+[M^4]^{2+}[Y]^{n-} \quad \text{(IIIj) where } n=3 \text{ and}$$

where $[A^1]^+$, $[A^2]^+$, and $[A^3]^+$ are each independently selected from the groups specified for $[A]^+$, $[Y]^{n-}$ is as defined under (A), and $[M^1]^+$, $[M^2]^+$, $[M^3]^+$ are each monovalent metal cations, $[M^4]^{2+}$ are divalent metal cations and $[M^5]^{3+}$ are trivalent metal cations.

The ionic liquids preferably have a melting point of less than 180° C. Additionally preferably, the melting point is within a range from −50° C. to 150° C., more preferably in the range from −20° C. to 120° C. and even more preferably less than 100° C.

The inventive ionic liquids are organic compounds, which means that at least one cation or an anion of the ionic liquid comprises an organic radical.

Compounds which are suitable for forming the cation $[A]^+$ of ionic liquids are known, for example, from DE 102 02 838 A1. For instance, such compounds may comprise oxygen atoms, phosphorus atoms, sulfur atoms or especially nitrogen atoms, for example at least one nitrogen atom, preferably 1-10 nitrogen atoms, more preferably 1-5, even more preferably 1-3 and especially 1-2 nitrogen atoms. It is optionally also possible for further heteroatoms such as oxygen, sulfur or phosphorus atoms to be present. The nitrogen atom is a suitable carrier of the positive charge in the cation of the ionic liquid, from which, in equilibrium, a proton or an alkyl radical can then be transferred to the anion in order to obtain an electrically uncharged molecule.

In the case that the nitrogen atom is the carrier of the positive charge in the cation of the ionic liquid, a cation can first be obtained in the course of synthesis of the ionic liquids by quaternization on the nitrogen atom, for instance of an amine or nitrogen heterocycle. The quaternization can be effected by protonating or alkylating the nitrogen atom. According to the alkylating reagent used, salts with different anions are obtained. In cases in which it is impossible to form the desired anion directly in the quaternization, this can be done in a further synthesis step. Proceeding, for example, from an ammonium halide, the halide can be reacted with a Lewis acid to form a complex anion from halide and Lewis acid. Alternatively, the exchange of a halide ion for the desired anion is possible. This can be done by adding a metal salt with precipitation of the metal halide formed, by means of an ion exchanger or by displacing the halide ion with a strong acid (to release the hydrohalic acid). Suitable processes are described, for example, in Angew. Chem. 2000, 112, p. 3926-3945, and the literature cited therein.

Suitable alkyl radicals with which the nitrogen atom in the amines or nitrogen heterocycles can be quaternized, for example, are $C_1$-$C_{18}$-alkyl, preferably $C_1$-$C_{10}$-alkyl, more preferably $C_1$-$C_6$-alkyl and most preferably methyl. The alkyl group may be unsubstituted or have one or more identical or different substituents.

Preference is given to those compounds which comprise at least one five- to six-membered heterocycle, especially a five-membered heterocycle, which has at least one nitrogen atom and optionally an oxygen or sulfur atom, particular preference being given to those compounds which comprise at least one five- or six-membered heterocycle which has one, two or three nitrogen atoms and a sulfur or an oxygen atom, very particular preference to those having two nitrogen atoms. Additionally preferred are aromatic heterocycles.

Particularly preferred compounds are those which have a molar mass less than 1000 g/mol, most preferably less than 500 g/mol.

Additionally preferred are those cations which are selected from the compounds of the formulae (IVa) to (IVw),

(IVa)

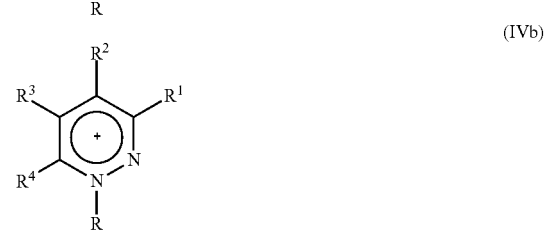

(IVb)

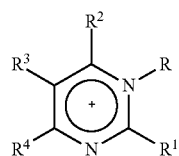
(IVc)
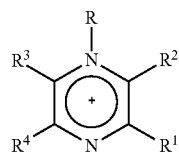
(IVd)
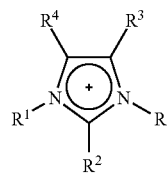
(IVe)
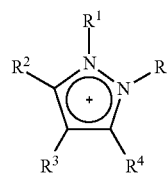
(IVf)
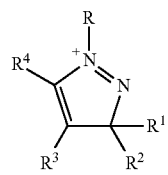
(IVg)
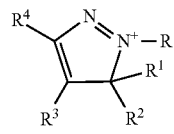
(IVg')
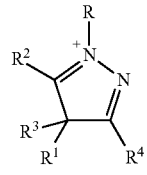
(IVh)
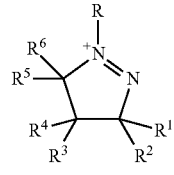
(IVi)
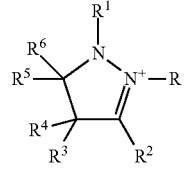
(IVj)
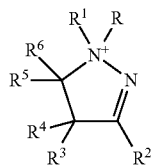
(IVj')
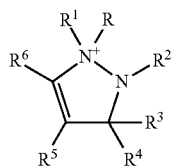
(IVk)
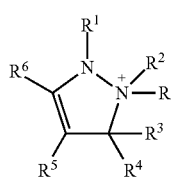
(IVk')
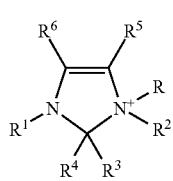
(IVl)
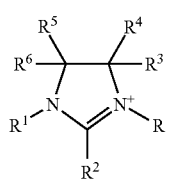
(IVm)
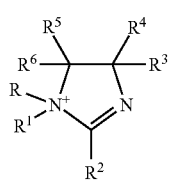
(IVm')
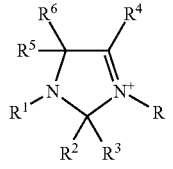
(IVn)
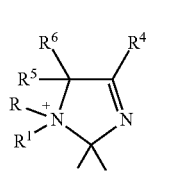
(IVn')
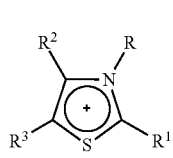
(IVo)

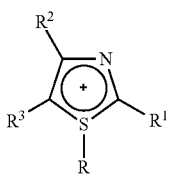 (IVo')

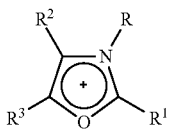 (IVp)

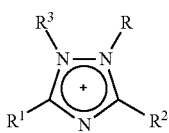 (IVq)

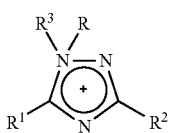 (IVq')

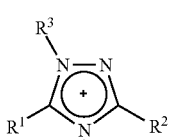 (IVq'')

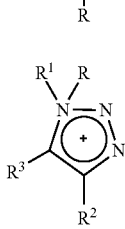 (IVr)

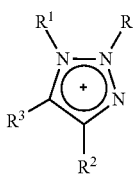 (IVr')

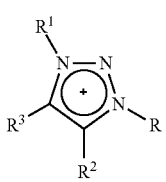 (IVr'')

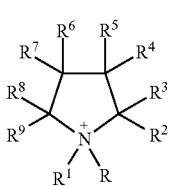 (IVs)

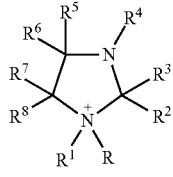 (IVt)

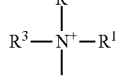 (IVu)

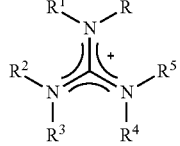 (IVv)

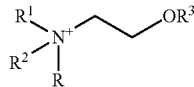 (IVw)

and oligomers which comprise these structures.

Further suitable cations are compounds of the general formulae (IVx) and (IVy)

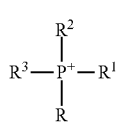 (IVx)

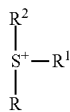 (IVy)

and oligomers which comprise this structure.

In the abovementioned formulae (IVa) to (IVy), the R radical is hydrogen, a carbon-comprising organic, saturated or unsaturated, acyclic or cyclic, aliphatic, aromatic or araliphatic radical which is unsubstituted or interrupted by 1 to 5 heteroatoms or functional groups or substituted and has 1 to 20 carbon atoms; and the $R^1$ to $R^9$ radicals are each independently hydrogen, a sulfo group or a carbon-comprising organic, saturated or unsaturated, acyclic or cyclic, aliphatic, aromatic or araliphatic radical which is unsubstituted or interrupted or substituted by 1 to 5 heteroatoms or functional groups and has 1 to 20 carbon atoms, where the $R^1$ to $R^9$ radicals which are bonded in the abovementioned formulae (IV) to a carbon atom (and not to a heteroatom) may additionally also be halogen or a functional group; or two adjacent radicals from the $R^1$ to $R^9$ series together are also a divalent, carbon-comprising organic, saturated or unsaturated, acyclic or cyclic, aliphatic, aromatic or araliphatic radical which is unsubstituted or interrupted or substituted by 1 to 5 heteroatoms or functional groups and has 1 to 30 carbon atoms.

Useful heteroatoms in the definition of the R and $R^1$ to $R^9$ radicals are in principle all heteroatoms which are capable of formally replacing a —$CH_2$—, a —CH═, a —C═ or a =C= group. When the carbon-comprising radical comprises heteroatoms, preference is given to oxygen, nitrogen, sulfur, phosphorus and silicon. Preferred groups include especially —O—, —S—, —SO—, —SO$_2$—, —NR'—, —N=, —PR'—, —PR'$_2$ and —SiR'$_2$—, where the R' radicals are the remaining part of the carbon-comprising radical. The $R^1$ to $R^9$ radicals may, in the cases in which they are bonded to a carbon atom (and not to a heteroatom) in the abovementioned formulae (IV), also be bonded directly via the heteroatom.

Useful functional groups are in principle all functional groups which may be bonded to a carbon atom or a heteroatom. Suitable examples include —OH (hydroxyl), =O (especially as a carbonyl group), —NH$_2$ (amino), —NHR', —NR$_2$'=NH (imino), —COOH (carboxyl), —CONH$_2$ (carboxamide), —SO$_3$H (sulfo) and —CN (cyano). Functional groups and heteroatoms may also be directly adjacent, and so combinations of a plurality of adjacent atoms, for instance —O— (ether), —S— (thioether), —COO— (ester), —CONH— (secondary amide) or —CONR'— (tertiary amide) are also included, for example di($C_1$-$C_4$-alkyl)amino, $C_1$-$C_4$-alkyloxycarbonyl or $C_1$-$C_4$-alkyloxy. The R' radicals are the remaining part of the carbon-comprising radical.

Halogens include fluorine, chlorine, bromine and iodine.

The R radical is preferably
  unbranched or branched, unsubstituted or mono- to polyhydroxyl-, -halogen-, -phenyl-, -cyano-, —$C_1$-$C_6$-alkoxycarbonyl- and/or —SO$_3$H-substituted $C_1$-$C_{18}$-alkyl with a total of 1 to 20 carbon atoms, for example methyl, ethyl, 1-propyl, 2-propyl, 1-butyl, 2-butyl, 2-methyl-1-propyl(isobutyl), 2-methyl-2-propyl(tert-butyl), 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,2-dimethyl-1-butyl, 2,3-dimethyl-1-butyl, 3,3-dimethyl-1-butyl, 2-ethyl-1-butyl, 2,3-dimethyl-2-butyl, 3,3-dimethyl-2-butyl, 1-heptyl, 1-octyl, 1-nonyl, 1-decyl, 1-undecyl, 1-dodecyl, 1-tetradecyl, 1-hexadecyl, 1-octadecyl, benzyl, 3-phenylpropyl, 2-hydroxyethyl, 2-cyanoethyl, 2-(methoxycarbonyl)ethyl, 2-(ethoxycarbonyl)ethyl, 2-(n-butoxycarbonyl)ethyl, trifluoromethyl, difluoromethyl, fluoromethyl, pentafluoroethyl, heptafluoropropyl, heptafluoroisopropyl, nonafluorobutyl, nonafluoroisobutyl, undecylfluoropentyl, undecylfluoroisopentyl, 6-hydroxyhexyl and sulfopropyl;
  glycols, butylene glycols and oligomers thereof having 1 to 100 units and a hydrogen or a $C_1$-$C_8$-alkyl as the end group, for example
    $R^A$O—(CHR$^B$—CH$_2$—O)$_n$—CHR$^B$—CH$_2$— or $R^A$O—(CH$_2$CH$_2$CH$_2$CH$_2$O)$_n$—CH$_2$CH$_2$CH$_2$CH$_2$O— where $R^A$ and $R^B$ are preferably each hydrogen, methyl or ethyl, and n is preferably 0 to 3, especially 3-oxabutyl, 3-oxapentyl, 3,6-dioxaheptyl, 3,6-dioxaoctyl, 3,6,9-trioxadecyl, 3,6,9-trioxaundecyl, 3,6,9,12-tetraoxatridecyl and 3,6,9,12-tetraoxatetradecyl;
  vinyl;
  1-propen-1-yl, 1-propen-2-yl and 1-propen-3-yl; and
  N,N-di-$C_1$-$C_6$-alkylamino, for example N,N-dimethylamino and N,N-diethylamino.

The R radical is more preferably unbranched and unsubstituted $C_1$-$C_{18}$-alkyl, for example methyl, ethyl, 1-propyl, 1-butyl, 1-pentyl, 1-hexyl, 1-heptyl, 1-octyl, 1-decyl, 1-dodecyl, 1-tetradecyl, 1-hexadecyl, 1-octadecyl, especially methyl, ethyl, 1-butyl and 1-octyl, and also CH$_3$O—(CH$_2$CH$_2$O)$_n$—CH$_2$CH$_2$— and CH$_3$CH$_2$O—(CH$_2$CH$_2$O)$_n$—CH$_2$CH$_2$— where n is 0 to 3.

The $R^1$ to $R^9$ radicals are preferably each independently
  hydrogen;
  halogen;
  a functional group;
  $C_1$-$C_{18}$-alkyl optionally substituted by functional groups, aryl, alkyl, aryloxy, alkyloxy, halogen, heteroatoms and/or heterocycles, and/or interrupted by one or more oxygen and/or sulfur atoms and/or one or more substituted or unsubstituted imino groups;
  $C_2$-$C_{18}$-alkenyl optionally substituted by functional groups, aryl, alkyl, aryloxy, alkyloxy, halogen, heteroatoms and/or heterocycles, and/or interrupted by one or more oxygen and/or sulfur atoms and/or one or more substituted or unsubstituted imino groups;
  $C_6$-$C_{12}$-aryl optionally substituted by functional groups, aryl, alkyl, aryloxy, alkyloxy, halogen, heteroatoms and/or heterocycles;
  $C_5$-$C_{12}$-cycloalkyl optionally substituted by functional groups, aryl, alkyl, aryloxy, alkyloxy, halogen, heteroatoms and/or heterocycles;
  $C_5$-$C_{12}$-cycloalkenyl optionally substituted by functional groups, aryl, alkyl, aryloxy, alkyloxy, halogen, heteroatoms and/or heterocycles; or
  a five- to six-membered heterocycle having oxygen, nitrogen and/or sulfur atoms, optionally substituted by functional groups, aryl, alkyl, aryloxy, alkyloxy, halogen, heteroatoms and/or heterocycles; or
  two adjacent radicals together with the atoms to which they are bonded are
    an unsaturated, saturated or aromatic ring optionally substituted by functional groups, aryl, alkyl, aryloxy, alkyloxy, halogen, heteroatoms and/or heterocycles, and optionally interrupted by one or more oxygen and/or sulfur atoms and/or one or more substituted or unsubstituted imino groups.

$C_1$-$C_{18}$-alkyl optionally substituted by functional groups, aryl, alkyl, aryloxy, alkyloxy, halogen, heteroatoms and/or heterocycles is preferably methyl, ethyl, 1-propyl, 2-propyl, 1-butyl, 2-butyl, 2-methyl-1-propyl(isobutyl), 2-methyl-2-propyl(tert-butyl), 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,2-dimethyl-1-butyl, 2,3-dimethyl-1-butyl, 3,3-dimethyl-1-butyl, 2-ethyl-1-butyl, 2,3-dimethyl-2-butyl, 3,3-dimethyl-2-butyl, heptyl, octyl, 2-ethylhexyl, 2,4,4-trimethylpentyl, 1,1,3,3-tetramethylbutyl, 1-nonyl, 1-decyl, 1-undecyl, 1-dodecyl, 1-tridecyl, 1-tetradecyl, 1-pentadecyl, 1-hexadecyl, 1-heptadecyl, 1-octadecyl, cyclopentylmethyl, 2-cyclopentylethyl, 3-cyclopentylpropyl, cyclohexylmethyl, 2-cyclohexylethyl, 3-cyclohexylpropyl, benzyl(phenylmethyl), diphenylmethyl (benzhydryl), triphenylmethyl, 1-phenylethyl, 2-phenylethyl, 3-phenylpropyl, α,α-dimethylbenzyl, p-tolylmethyl, 1-(p-butylphenyl)ethyl, p-chlorobenzyl, 2,4-dichlorobenzyl, p-methoxybenzyl, m-ethoxybenzyl, 2-cyanoethyl, 2-cyanopropyl, 2-methoxycarbonylethyl, 2-ethoxycarbonylethyl, 2-butoxycarbonylpropyl, 1,2-di-(methoxycarbonyl)ethyl, methoxy, ethoxy, formyl, 1,3-dioxolan-2-yl, 1,3-dioxan-2-yl, 2-methyl-1,3-dioxolan-2-yl, 4-methyl-1,3-dioxolan-2-yl, 2-hydroxyethyl, 2-hydroxypropyl, 3-hydroxypropyl, 4-hydroxybutyl, 6-hydroxyhexyl, 2-aminoethyl, 2-aminopropyl, 3-aminopropyl, 4-aminobutyl, 6-aminohexyl, 2-methylaminoethyl, 2-methylaminopropyl, 3-methylaminopropyl, 4-methylaminobutyl, 6-methylaminohexyl, 2-dimethylaminoethyl, 2-dimethylaminopropyl, 3-dimethylaminopropyl, 4-dimethylaminobutyl, 6-dimethylaminohexyl, 2-hydroxy-2,2-dimethylethyl, 2-phenoxyethyl, 2-phenoxypropyl, 3-phenoxypropyl, 4-phenoxybutyl, 6-phenoxyhexyl, 2-methoxyethyl, 2-methoxypropyl, 3-methoxypropyl, 4-methoxybutyl, 6-methoxyhexyl, 2-ethoxyethyl, 2-ethoxypropyl, 3-ethoxypropyl, 4-ethoxybutyl, 6-ethoxyhexyl, acetyl, $C_nF_{2(n-a)+(1-b)}H_{2a+b}$ where n is 1 to 30, $0 \leq a \leq n$ and b=0 or 1 (for example $CF_3$, $C_2F_5$, $CH_2CH_2-C_{(n-2)}F_{2(n-2)+1}$, $C_6F_{13}$, $C_8F_{17}$, $C_{10}F_{21}$, $C_{12}F_{25}$), chloromethyl, 2-chloroethyl, trichloromethyl, 1,1-dimethyl-2-chloroethyl, methoxymethyl, 2-butoxyethyl, diethoxymethyl, diethoxyethyl, 2-isopropoxyethyl, 2-butoxypropyl, 2-octyloxyethyl, 2-methoxyisopropyl, 2-(methoxycarbonyl)ethyl, 2-(ethoxycarbonyl) ethyl, 2-(n-butoxycarbonyl)ethyl, butylthiomethyl, 2-dodecylthioethyl, 2-phenylthioethyl, 5-hydroxy-3-oxapentyl, 8-hydroxy-3,6-dioxaoctyl, 11-hydroxy-3,6,9-trioxaundecyl, 7-hydroxy-4-oxaheptyl, 11-hydroxy-4,8-dioxaundecyl, 15-hydroxy-4,8,12-trioxapentadecyl, 9-hydroxy-5-oxanonyl, 14-hydroxy-5,10-dioxatetradecyl, 5-methoxy-3-oxapentyl, 8-methoxy-3,6-dioxaoctyl, 11-methoxy-3,6,9-trioxaundecyl, 7-methoxy-4-oxaheptyl, 11-methoxy-4,8-dioxaundecyl, 15-methoxy-4,8,12-trioxapentadecyl, 9-methoxy-5-oxanonyl, 14-methoxy-5,10-dioxatetradecyl, 5-ethoxy-3-oxapentyl, 8-ethoxy-3,6-dioxaoctyl, 11-ethoxy-3,6,9-trioxaundecyl, 7-ethoxy-4-oxaheptyl, 11-ethoxy-4,8-dioxaundecyl, 15-ethoxy-4,8,12-trioxapentadecyl, 9-ethoxy-5-oxanonyl or 14-ethoxy-5,10-oxatetradecyl.

$C_2$-$C_{18}$-Alkenyl optionally substituted by functional groups, aryl, alkyl, aryloxy, alkyloxy, halogen, heteroatoms and/or heterocycles and/or interrupted by one or more oxygen and/or sulfur atoms and/or one or more substituted or unsubstituted imino groups is preferably vinyl, 2-propenyl, 3-butenyl, cis-2-butenyl, trans-2-butenyl or $C_nF_{2(n-a)-(1-b)}H_{2a-b}$ where $n \leq 30$, $0 \leq a \leq n$ and b=0 or 1.

$C_6$-$C_{12}$-Aryl optionally substituted by functional groups, aryl, alkyl, aryloxy, alkyloxy, halogen, heteroatoms and/or heterocycles is preferably phenyl, tolyl, xylyl, α-naphthyl, β-naphthyl, 4-diphenylyl, chlorophenyl, dichlorophenyl, trichlorophenyl, difluorophenyl, methylphenyl, dimethylphenyl, trimethylphenyl, ethylphenyl, diethylphenyl, isopropylphenyl, tert-butylphenyl, dodecylphenyl, methoxyphenyl, dimethoxyphenyl, ethoxyphenyl, hexyloxyphenyl, methylnaphthyl, isopropylnaphthyl, chloronaphthyl, ethoxynaphthyl, 2,6-dimethylphenyl, 2,4,6-trimethylphenyl, 2,6-dimethoxyphenyl, 2,6-dichlorophenyl, 4-bromophenyl, 2-nitrophenyl, 4-nitrophenyl, 2,4-dinitrophenyl, 2,6-dinitrophenyl, 4-dimethylaminophenyl, 4-acetylphenyl, methoxyethylphenyl, ethoxymethylphenyl, methylthiophenyl, isopropylthiophenyl or tert-butylthiophenyl or $C_6F_{(5-a)}H_a$ where $0 \leq a \leq 5$.

$C_5$-$C_{12}$-Cycloalkyl optionally substituted by functional groups, aryl, alkyl, aryloxy, alkyloxy, halogen, heteroatoms and/or heterocycles is preferably cyclopentyl, cyclohexyl, cyclooctyl, cyclododecyl, methylcyclopentyl, dimethylcyclopentyl, methylcyclohexyl, dimethylcyclohexyl, diethylcyclohexyl, butylcyclohexyl, methoxycyclohexyl, dimethoxycyclohexyl, diethoxycyclohexyl, butylthiocyclohexyl, chlorocyclohexyl, dichlorocyclohexyl, dichlorocyclopentyl, $C_nF_{2(n-a)-(1-b)}H_{2a-b}$ where $n \leq 30$, $0 \leq a \leq n$ and b=0 or 1, or a saturated or unsaturated bicyclic system such as norbornyl or norbornenyl.

$C_5$- to $C_{12}$-cycloalkenyl optionally substituted by functional groups, aryl, alkyl, aryloxy, alkyloxy, halogen, heteroatoms and/or heterocycles is preferably 3-cyclopentenyl, 2-cyclohexenyl, 3-cyclohexenyl, 2,5-cyclohexadienyl or $C_nF_{2(n-a)-3(1-b)}H_{2a-3b}$ where $n \leq 30$, $0 \leq a \leq n$ and b=0 or 1.

A five- or six-membered, oxygen-, nitrogen- and/or sulfur-comprising heterocycle optionally substituted by functional groups, aryl, alkyl, aryloxy, alkyloxy, halogen, heteroatoms and/or heterocycles is preferably furyl, thiophenyl, pyrryl, pyridyl, indolyl, benzoxazolyl, dioxolyl, dioxyl, benzimidazolyl, benzthiazolyl, dimethylpyridyl, methylquinolyl, dimethylpyrryl, methoxyfuryl, dimethoxypyridyl or difluoropyridyl.

When two adjacent radicals together form an unsaturated, saturated or aromatic ring optionally substituted by functional groups, aryl, alkyl, aryloxy, alkyloxy, halogen, heteroatoms and/or heterocycles and optionally interrupted by one or more oxygen and/or sulfur atoms and/or one or more substituted or unsubstituted imino groups, the ring is preferably 1,3-propylene, 1,4-butylene, 1,5-pentylene, 2-oxa-1,3-propylene, 1-oxa-1,3-propylene, 2-oxa-1,3-propylene, 1-oxa-1,3-propenylene, 3-oxa-1,5-pentylene, 1-aza-1,3-propenylene, 1-$C_1$-$C_4$-alkyl-1-aza-1,3-propenylene, 1,4-buta-1,3-dienylene, 1-aza-1,4-buta-1,3-dienylene or 2-aza-1,4-buta-1,3-dienylene.

When the abovementioned radicals comprise oxygen and/or sulfur atoms and/or substituted or unsubstituted imino groups, the number of oxygen and/or sulfur atoms and/or imino groups is not restricted. In general, there will be no more than 5 in the radical, preferably no more than 4 and very particularly preferably no more than 3.

When the abovementioned radicals comprise heteroatoms, there is generally at least one carbon atom, preferably at least two carbon atoms, between any two heteroatoms.

The $R^1$ to $R^9$ radicals are more preferably each independently hydrogen;

unbranched or branched $C_1$-$C_{18}$-alkyl which is unsubstituted or substituted by one or more hydroxyl, halogen, phenyl, cyano, $C_1$-$C_6$-alkoxycarbonyl and/or $SO_3H$ and has a total of from 1 to 20 carbon atoms, for example methyl, ethyl, 1-propyl, 2-propyl, 1-butyl, 2-butyl, 2-methyl-1-propyl(isobutyl), 2-methyl-2-propyl(tertbutyl), 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,2-dimethyl-1-butyl, 2,3-dimethyl-1-butyl, 3,3-dimethyl-1-butyl, 2-ethyl-1-butyl, 2,3-dimethyl-2-butyl, 3,3-dimethyl-2-butyl, 1-heptyl, 1-octyl, 1-nonyl, 1-decyl, 1-undecyl, 1-dodecyl, 1-tetradecyl, 1-hexadecyl, 1-octadecyl, benzyl, 3-phenylpropyl, 2-hydroxyethyl, 2-cyanoethyl, 2-(methoxycarbonyl)ethyl, 2-(ethoxycarbonyl) ethyl, 2-(n-butoxycarbonyl)ethyl, trifluoromethyl, difluoromethyl, fluoromethyl, pentafluoroethyl, heptafluoropropyl, heptafluoroisopropyl, nonafluorobutyl, nonafluoroisobutyl, undecylfluoropentyl, undecylfluoroisopentyl, 6-hydroxyhexyl and sulfopropyl;

glycols, butylene glycols and oligomers thereof having from 1 to 100 units and a hydrogen or a $C_1$-$C_8$-alkyl as the end group, for example $R^AO-(CHR^B-CH_2-O)_n-CHR^B-CH_2-$ or $R^AO-(CH_2CH_2CH_2CH_2O)_n-CH_2CH_2CH_2CH_2O-$ where $R^A$ and $R^B$ are preferably each hydrogen, methyl or ethyl and n is preferably 0 to 3, especially 3-oxabutyl, 3-oxapentyl, 3,6-dioxaheptyl, 3,6-dioxaoctyl, 3,6,9-trioxadecyl, 3,6,9-trioxaundecyl, 3,6,9,12-tetraoxatridecyl and 3,6,9,12-tetraoxatetradecyl;

vinyl;
1-propen-1-yl, 1-propen-2-yl and 1-propen-3-yl; and
N,N-di-$C_1$-$C_5$-alkylamino, for example N,N-dimethylamino and N,N-diethylamino.

The $R^1$ to $R^9$ radicals are most preferably each independently hydrogen or $C_1$-$C_{18}$-alkyl, for example methyl, ethyl, 1-butyl, 1-pentyl, 1-hexyl, 1-heptyl, 1-octyl, phenyl, 2-hydroxyethyl, 2-cyanoethyl, 2-(methoxycarbonyl)ethyl, 2-(ethoxycarbonyl)ethyl, 2-(n-butoxycarbonyl)ethyl, N,N-dimethylamino, N,N-diethylamino, chlorine or $CH_3O$—$(CH_2CH_2O)_n$—$CH_2CH_2$— and $CH_3CH_2O$—$(CH_2CH_2O)_n$—$CH_2CH_2$— where n is 0 to 3.

The pyridinium ions (IVa) used are most preferably those in which
  one of the $R^1$ to $R^5$ radicals is methyl, ethyl or chlorine and the remaining $R^1$ to $R^5$ radicals are each hydrogen;
  $R^3$ is dimethylamino and the remaining $R^1$, $R^2$, $R^4$ and $R^5$ radicals are each hydrogen;
  all $R^1$ to $R^5$ radicals are hydrogen;
  $R^2$ is carboxyl or carboxamide and the remaining $R^1$, $R^2$, $R^4$ and $R^5$ radicals are each hydrogen; or
  $R^1$ and $R^2$ or $R^2$ and $R^3$ together are 1,4-buta-1,3-dienylene and the remaining $R^1$, $R^2$, $R^4$ and $R^5$ radicals are each hydrogen;
and especially those in which
  $R^1$ to $R^5$ are each hydrogen; or
  one of the $R^1$ to $R^5$ radicals is methyl or ethyl and the remaining $R^1$ to $R^5$ radicals are each hydrogen.

Very particularly preferred pyridinium ions (IVa) include 1-methylpyridinium, 1-ethylpyridinium, 1-(1-butyl)pyridinium, 1-(1-hexyl)pyridinium, 1-(1-octyl)pyridinium, 1-(1-hexyl)pyridinium, 1-(1-octyl)pyridinium, 1-(1-dodecyl)pyridinium, 1-(1-tetradecyl)-pyridinium, 1-(1-hexadecyl)pyridinium, 1,2-dimethylpyridinium, 1-ethyl-2-methylpyridinium, 1-(1-butyl)-2-methylpyridinium, 1-(1-hexyl)-2-methylpyridinium, 1-(1-octyl)-2-methylpyridinium, 1-(1-dodecyl)-2-methylpyridinium, 1-(1-tetradecyl)-2-methylpyridinium, 1-(1-hexadecyl)-2-methylpyridinium, 1-methyl-2-ethylpyridinium, 1,2-diethylpyridinium, 1-(1-butyl)-2-ethylpyridinium, 1-(1-hexyl)-2-ethylpyridinium, 1-(1-octyl)-2-ethylpyridinium, 1-(1-dodecyl)-2-ethylpyridinium, 1-(1-tetradecyl)-2-ethylpyridinium, 1-(1-hexadecyl)-2-ethylpyridinium, 1,2-dimethyl-5-ethylpyridinium, 1,5-diethyl-2-methylpyridinium, 1-(1-butyl)-2-methyl-3-ethylpyridinium, 1-(1-hexyl)-2-methyl-3-ethylpyridinium and 1-(1-octyl)-2-methyl-3-ethylpyridinium, 1-(1-dodecyl)-2-methyl-3-ethylpyridinium, 1-(1-tetradecyl)-2-methyl-3-ethylpyridinium and 1-(1-hexadecyl)-2-methyl-3-ethylpyridinium.

The pyridazinium ions (IVb) used are most preferably those in which
  $R^1$ to $R^4$ are each hydrogen; or
  one of the $R^1$ to $R^4$ radicals is methyl or ethyl and the remaining $R^1$ to $R^4$ radicals are each hydrogen.

The pyrimidinium ions (IVc) used are most preferably those in which
  $R^1$ is hydrogen, methyl or ethyl and $R^2$ to $R^4$ are each independently hydrogen or methyl; or
  $R^1$ is hydrogen, methyl or ethyl, $R^2$ and $R^4$ are each methyl and $R^3$ is hydrogen.

The pyrazinium ions (IVd) used are most preferably those in which
  $R^1$ is hydrogen, methyl or ethyl and $R^2$ to $R^4$ are each independently hydrogen or methyl;
  $R^1$ is hydrogen, methyl or ethyl, $R^2$ and $R^4$ are each methyl and $R^3$ is hydrogen;
  $R^1$ to $R^4$ are each methyl; or
  $R^1$ to $R^4$ are each hydrogen.

The imidazolium ions (IVe) used are most preferably those in which
  $R^1$ is hydrogen, methyl, ethyl, 1-propyl, 1-butyl, 1-pentyl, 1-hexyl, 1-octyl, 2-hydroxyethyl or 2-cyanoethyl and $R^2$ to $R^4$ are each independently hydrogen, methyl or ethyl.

Very particularly preferred imidazolium ions (IVe) include 1-methylimidazolium, 1-ethylimidazolium, 1-(1-butyl)imidazolium, 1-(1-octyl)imidazolium, 1-(1-dodecyl)imidazolium, 1-(1-tetradecyl)imidazolium, 1-(1-hexadecyl)imidazolium, 1,3-dimethylimidazolium, 1-ethyl-3-methylimidazolium, 1-(1-butyl)-3-methylimidazolium, 1-(1-butyl)-3-ethylimidazolium, 1-(1-hexyl)-3-methylimidazolium, 1-(1-hexyl)-3-ethylimidazolium, 1-(1-hexyl)-3-butylimidazolium, 1-(1-octyl)-3-methylimidazolium, 1-(1-octyl)-3-ethylimidazolium, 1-(1-octyl)-3-butylimidazolium, 1-(1-dodecyl)-3-methylimidazolium, 1-(1-dodecyl)-3-ethylimidazolium, 1-(1-dodecyl)-3-butylimidazolium, dodecyl)-3-octylimidazolium, 1-(1-tetradecyl)-3-methylimidazolium, 1-(1-tetradecyl)-3-ethylimidazolium, 1-(1-tetradecyl)-3-butylimidazolium, 1-(1-tetradecyl)-3-octylimidazolium, 1-(1-hexadecyl)-3-methylimidazolium, 1-(1-hexadecyl)-3-ethylimidazolium, 1-(1-hexadecyl)-3-butylimidazolium, 1-(1-hexadecyl)-3-octylimidazolium, 1,2-dimethyl-imidazolium, 1,2,3-trimethylimidazolium, 1-ethyl-2,3-dimethylimidazolium, 1-(1-butyl)-2,3-dimethylimidazolium, 1-(1-hexyl)-2,3-dimethylimidazolium, 1-(1-octyl)-2,3-di-methylimidazolium, 1,4-dimethylimidazolium, 1,3,4-trimethylimidazolium, 1,4-dimethyl-3-ethylimidazolium, 3-butylimidazolium, 1,4-dimethyl-3-octylimidazolium, 1,4,5-trimethylimidazolium, 1,3,4,5-tetramethylimidazolium, 1,4,5-trimethyl-3-ethyl-imidazolium, 1,4,5-trimethyl-3-butylimidazolium, 1,4,5-trimethyl-3-octylimidazolium, and 1-(prop-1-en-3-yl)-3-methylimidazolium.

The pyrazolium ions (IVf), (IVg) and (IVg') used are most preferably those in which
  $R^1$ is hydrogen, methyl or ethyl and $R^2$ to $R^4$ are each independently hydrogen or methyl.

The pyrazolium ions (IVh) used are most preferably those in which
  $R^1$ to $R^4$ are each independently hydrogen or methyl.

The 1-pyrazolinium ions (IVi) used are most preferably those in which
  $R^1$ to $R^6$ are each independently hydrogen or methyl.

The 2-pyrazolinium ions (IVj) and (IVj') used are most preferably those in which
  $R^1$ is hydrogen, methyl, ethyl or phenyl and $R^2$ to $R^6$ are each independently hydrogen or methyl.

The 3-pyrazolinium ions (IVk) and (IVk') used are most preferably those in which
  $R^1$ and $R^2$ are each independently hydrogen, methyl, ethyl or phenyl and $R^3$ to $R^6$ are each independently hydrogen or methyl.

The imidazolinium ions (IVl) used are most preferably those in which
  $R^1$ and $R^2$ are each independently hydrogen, methyl, ethyl, 1-butyl or phenyl, $R^3$ and $R^4$ are each independently hydrogen, methyl or ethyl and $R^5$ and $R^6$ are each independently hydrogen or methyl.

The imidazolinium ions (IVm) and (IVm') used are most preferably those in which
  $R^1$ and $R^2$ are each independently hydrogen, methyl or ethyl and $R^3$ to $R^6$ are each independently hydrogen or methyl.

The imidazolinium ions (IVn) and (IVn') used are most preferably those in which
$R^1$ to $R^3$ are each independently hydrogen, methyl or ethyl and $R^4$ to $R^6$ are each independently hydrogen or methyl.

The thiazolium ions (IVo) and (IVo') and oxazolium ions (IVp) used are most preferably those in which
$R^1$ is hydrogen, methyl, ethyl or phenyl and $R^2$ and $R^3$ are each independently hydrogen or methyl.

The 1,2,4-triazolium ions (IVq), (IVq') and (IVq") used are most preferably those in which
$R^1$ and $R^2$ are each independently hydrogen, methyl, ethyl or phenyl and $R^3$ is hydrogen, methyl or phenyl.

The 1,2,3-triazolium ions (IVr), (IVr') and (IVr") used are most preferably those in which
$R^1$ is hydrogen, methyl or ethyl and $R^2$ and $R^3$ are each independently hydrogen or methyl or $R^2$ and $R^3$ together are 1,4-buta-1,3-dienylene.

The pyrrolidinium ions (IVs) used are most preferably those in which
$R^1$ is hydrogen, methyl, ethyl or phenyl and $R^2$ to $R^9$ are each independently hydrogen or methyl.

The imidazolidinium ions (IVt) used are most preferably those in which
$R^1$ and $R^4$ are each independently hydrogen, methyl, ethyl or phenyl and $R^2$ and $R^3$ and also $R^5$ to $R^8$ are each independently hydrogen or methyl.

The ammonium ions (IVu) used are most preferably those in which
$R^1$ to $R^3$ are each independently $C_1$-$C_{18}$-alkyl; or
$R^1$ and $R^2$ together are 1,5-pentylene or 3-oxa-1,5-pentylene and $R^3$ is $C_1$-$C_{18}$-alkyl, 2-hydroxyethyl or 2-cyanoethyl.

Very particularly preferred ammonium ions (IVu) include trimethylammonium, triethylammonium, dimethylethylammonium, diethylmethylammonium, tetramethylammonium.

Examples of the tertiary amines from which the quaternary ammonium ions of the general formula (IVu) derive by quaternization by the R radicals mentioned are trimethylamine, triethylamine, tri-n-propylamine, tri-n-butylamine, diethylmethylamine, dimethylethylamine, triisopropylamine, isopropyldiethylamine, diisopropylethylamine, diethyl-n-butylamine, diethyl-tert-butylamine, diethyl-n-pentylamine, diethylhexylamine, diethyloctylamine, diethyl-(2-ethylhexyl)amine, di-n-propylbutylamine, di-n-propyl-n-pentylamine, di-n-propylhexylamine, di-n-propyloctylamine, di-n-propyl-(2-ethyl-hexyl)amine, diisopropylethylamine, diisopropyl-n-propylamine, diisopropylbutylamine, diisopropylpentylamine, diisopropylhexylamine, diisopropyloctylamine, diisopropyl(2-ethylhexyl)amine, di-n-butylethylamine, di-n-butyl-n-propylamine, di-n-butyl-n-pentylamine, di-n-butylhexylamine, di-n-butyloctylamine, di-n-butyl(2-ethylhexyl)amine, N-n-butylpyrrolidine, N-sec-butylpyrrolidine, N-tert-butylpyrrolidine, N-n-pentylpyrrolidine, N,N-dimethylcyclohexylamine, N,N-diethylcyclohexylamine, N,N-di-n-butylcyclohexylamine, N-n-propylpiperidine, N-isopropylpiperidine, N-n-butylpiperidine, N-sec-butylpiperidine, N-tert-butylpiperidine, N-n-pentylpiperidine, N-n-butylmorpholine, N-sec-butylmorpholine, N-tert-butylmorpholine, N-n-pentylmorpholine, N-benzyl-N-ethylaniline, N-benzyl-N-n-propylaniline, N-benzyl-N-isopropylaniline, N-benzyl-N-n-butylaniline, N,N-dimethyl-p-toluidine, N,N-diethyl-p-toluidine, N,N-di-n-butyl-p-toluidine, diethylbenzylamine, di-n-propylbenzylamine, di-n-butylbenzylamine, diethylphenylamine, di-n-propylphenylamine and di-n-butylphenylamine.

Preferred quaternary ammonium salts of the general formula (IVu) are those which can be derived from the following tertiary amines by quaternization with the R radicals mentioned: dimethylamine, trimethylamine, diethylamine, triethylamine, dimethylethylamine, diethyl-tert-butylamine, diisopropylethylamine, tripropylamine, tributylamine.

Particularly preferred tertiary amines are trimethylamine and triethylamine.

The guanidinium ions (IVv) used are most preferably those in which
$R^1$ to $R^5$ are each methyl.

A very particularly preferred guanidinium ion (IVv) is N,N,N',N',N",N"-hexamethylguanidinium.

The cholinium ions (IVw) used are most preferably those in which
$R^1$ and $R^2$ are each independently methyl, ethyl, 1-butyl or 1-octyl and $R^3$ is hydrogen, methyl, ethyl, acetyl, $-SO_2OH$ or $-PO(OH)_2$;
$R^1$ is methyl, ethyl, 1-butyl or 1-octyl, $R^2$ is a $-CH_2-CH_2-OR^4$ group and $R^3$ and $R^4$ are each independently hydrogen, methyl, ethyl, acetyl, $-SO_2OH$ or $-PO(OH)_2$; or
$R^1$ is a $-CH_2-CH_2-OR^4$ group, $R^2$ is a $-CH_2-CH_2-OR^5$ group and $R^3$ to $R^5$ are each independently hydrogen, methyl, ethyl, acetyl, $-SO_2OH$ or $-PO(OH)_2$.

Particularly preferred cholinium ions (IVw) are those in which $R^3$ is selected from among hydrogen, methyl, ethyl, acetyl, 5-methoxy-3-oxapentyl, 8-methoxy-3,6-dioxaoctyl, 11-methoxy-3,6,9-trioxaundecyl, 7-methoxy-4-oxaheptyl, 11-methoxy-4,8-dioxaundecyl, 15-methoxy-4,8,12-trioxapentadecyl, 9-methoxy-5-oxanonyl, 14-methoxy-5,10-oxatetradecyl, 5-ethoxy-3-oxapentyl, 8-ethoxy-3,6-dioxaoctyl, 11-ethoxy-3,6,9-trioxaundecyl, 7-ethoxy-4-oxaheptyl, 11-ethoxy-4,8-dioxaundecyl, 15-ethoxy-4,8,12-trioxapentadecyl, 9-ethoxy-5-oxanonyl or 14-ethoxy-5,10-oxatetradecyl.

The phosphonium ions (IVx) used are most preferably those in which
$R^1$ to $R^3$ are each independently $C_1$-$C_{18}$-alkyl, especially butyl, isobutyl, 1-hexyl or 1-octyl.

Among the abovementioned heterocyclic cations, preference is given to the pyridinium ions, pyrazolinium ions, pyrazolium ions and the imidazolinium ions and the imidazolium ions. Preference is also given to ammonium ions.

Especially preferred are 1-methylpyridinium, 1-ethylpyridinium, 1-(1-butyl)pyridinium, 1-(1-hexyl)pyridinium, 1-(1-octyl)pyridinium, 1-(1-hexyl)pyridinium, 1-(1-octyl)pyridinium, 1-(1-dodecyl)pyridinium, 1-(1-tetradecyl)pyridinium, 1-(1-hexadecyl)pyridinium, 1,2-dimethylpyridinium, 1-ethyl-2-methylpyridinium, 1-(1-butyl)-2-methylpyridinium, 1-(1-hexyl)-2-methylpyridinium, 1-(1-octyl)-2-methylpyridinium, 1-(1-dodecyl)-2-methylpyridinium, 1-(1-tetradecyl)-2-methylpyridinium, 1-(1-hexadecyl)-2-methylpyridinium, 1-methyl-2-ethylpyridinium, 1,2-diethylpyridinium, 1-(1-butyl)-2-ethylpyridinium, 1-(1-hexyl)-2-ethylpyridinium, 1-(1-octyl)-2-ethylpyridinium, 1-(1-dodecyl)-2-ethylpyridinium, 1-(1-tetradecyl)-2-ethylpyridinium, 1-(1-hexadecyl)-2-ethylpyridinium, 1,2-dimethyl-5-ethylpyridinium, 1,5-diethyl-2-methylpyridinium, 1-(1-butyl)-2-methyl-3-ethylpyridinium, 1-(1-hexyl)-2-methyl-3-ethylpyridinium, 1-(1-octyl)-2-methyl-3-ethylpyridinium, 1-(1-dodecyl)-2-methyl-3-ethylpyridinium, 1-(1-tetradecyl)-2-methyl-3-ethylpyridinium, 1-(1-hexadecyl)-2-methyl-3-ethylpyridinium, 1-methyl-imidazolium, 1-ethylimidazolium, 1-(1-butyl)imidazolium, 1-(1-octyl)imidazolium, 1-(1-dodecyl)imidazolium, 1-(1-tetradecyl)imidazolium, 1-(1-hexadecyl)imidazolium, 1,3-dimethylimidazolium, 1-ethyl-3-methylimidazolium, 1-(1-butyl)-3-methylimidazolium, 1-(1-hexyl)-3-methylimidazolium, 1-(1-octyl)-3-methylimidazolium, 1-(1-dodecyl)-3-methylimidazolium, 1-(1-tetradecyl)-3-methylimidazolium, 1-(1-hexadecyl)-3-methylimidazolium, 1,2-dimethylimidazolium, 1,2,3-trimethylimidazolium, 1-ethyl-2,3-dimethylimidazolium, 1-(1-butyl)-2,3-dimethylimidazolium, 1-(1-hexyl)-2,3-dimethylimidazolium and 1-(1-octyl)-2,3-dimethylimidazolium, 1,4-dimethylimidazolium, 1,3,4-trimethylimidazolium, 1,4-dimethyl-3-ethylimidazolium, 3-butylimidazolium, 1,4-dimethyl-3-octylimidazolium, 1,4,5-trimethylimidazolium, 1,3,4,5-tetramethylimidazolium, 1,4,5-trimethyl-3-ethylimidazolium, 1,4,5-trimethyl-3-butylimidazolium, 1,4,5-trimethyl-3-octylimidazolium and 1-(prop-1-en-3-yl)-3-methylimidazolium.

The metal cations $[M^1]^+$, $[M^2]^+$, $[M^3]^+$, $[M^4]^{2+}$ and $[M^5]^{3+}$ mentioned in the formulae (IIIa) to (IIIj) are generally metal cations of groups 1, 2, 6, 7, 8, 9, 10, 11, 12 and 13, of the periodic table. Suitable metal cations are, for example, $Li^+$, $Na^+$, $K^+$, $Cs^+$, $Mg^{2+}$, $Ca^{2+}$, $Ba^{2+}$, $Cr^{3+}$, $Fe^{2+}$, $Fe^{3+}$, $Co^{2+}$, $Ni^{2+}$, $Cu^{2+}$, $Ag^+$, $Zn^{2+}$ and $Al^{3+}$.

The organic cation is more preferably an ammonium ion, optionally $C_{1-4}$-alkyl-substituted pyridinium ion or optionally $C_{1-4}$-alkyl-substituted imidazolium ion.

The organic cation is most preferably a trimethylammonium ion, triethylammonium ion, unsubstituted pyridinium ion or 1-ethyl-3-methylimidazolium ion.

The anion of the ionic liquids used in accordance with the invention is selected from superacidic aluminum trichloride-Lewis base adducts. Aluminum trichloride ($AlCl_3$) is a Lewis acid.

In the context of the present invention, the expression "superacidic aluminum trichloride-Lewis base adducts" refers to those aluminum trichloride-Lewis base adducts which, in protonated form, have a $pK_a$ which is less than that of a strong acid or less than or equal to the $pK_a$ of an extremely strong acid. The superacidic aluminum trichloride-Lewis base adducts used in accordance with the invention preferably have, in protonated form, a $pK_a$ of $<-7$, i.e. a smaller $pK_a$ than HCl.

In the context of the present invention, the expression "aluminum trichloride-Lewis base adduct" refers to complex anions which are formed by the addition of an anion, especially of a chloride or bromide, onto the Lewis acid aluminum trichloride. The addition products may also form adducts with one or two further (identical or different) Lewis acid molecules.

Typically, suitable Lewis acid-Lewis base adducts are selected from compounds of the formula $[Met_aZ_b]^-$, in which the value of b corresponds to the product of oxidation number of the metal or semimetal Met and the index a, plus 1, i.e. $b=a\cdot Ox+1$, where Ox is the oxidation number of the metal or semimetal. Typically, a has a value in the range from 1 to 3. Preferably, a in the Lewis acid-Lewis base adducts is 2 or 3.

When a is 2 or 3, the metals or semimetals Met present in the Lewis acid-Lewis base adduct may be the same or different. Lewis acid-Lewis base adducts with different metals form, for example, when a Lewis acid-Lewis base adduct first forms from a Lewis acid and a halide ion, and is then reacted with a further Lewis acid other than the first Lewis acid to form an adduct. Preferably, however, all Met present in the Lewis acid-Lewis base adduct $[Met_aZ_b]^-$ are the same, and are Al.

In the Lewis acid-Lewis base adduct of the formula $[Met_aZ_b]^-$, Z may be the same or different. Lewis acid-Lewis base adducts with mixed Z are obtained, for example, when, as described above, the Lewis acid-Lewis base adduct forms from two different Lewis acids. Alternatively, it is obtained when Lewis acids with mixed halogen atoms are used, or when the halide ion which functions as a Lewis base is different than the halogen atom of the Lewis acid. All Z present in the Lewis acid-Lewis base adduct of the formula $[Met_aZ_b]^-$ are especially the same; Z is especially chlorine or bromine.

Examples of suitable Lewis bases are $Cl^-$, $Br^-$, $AlCl_4^-$, $AlBrCl_3^-$, $Al_2BrCl_6^-$, $Al_3Cl_{10}^-$, $Al_3BrCl_9^-$, $BCl_4^-$, $BBr_4^-$, $TiCl_5^-$, $VCl_6^-$, $FeCl_4^-$, $FeBr_4^-$, $Fe_2Cl_7^-$, $Fe_3Cl_{10}^-$, $ZnCl_3^-$, $ZnBr_3^-$, $CuCl_2^-$, $CuBr_2^-$, $CuCl_3^-$, $CuBr_3^-$, $NbCl_6^-$, $SnCl_3^-$, $SnBr_3^-$, $SnCl_5^-$, $SnBr_5^-$ and $(CF_3SO_2)_2N^-$.

Preferred Lewis bases are $AlCl_4^-$, $Al_2Cl_7^-$, $BCl_4^-$, $BBr_4^-$, $TiCl_5^-$, $FeCl_4^-$, $FeBr_4^-$, $Fe_2Cl_7^-$ and $Fe_3Cl_{10}^-$.

Accordingly, the anion of the ionic liquid is, for example, $AlCl_4^-$, $AlBrCl_3^-$, $Al_2Cl_7^-$, $Al_2BrCl_6^-$, $Al_3Cl_{10}^-$, $Al_3BrCl_9^-$ or $(CF_3SO_2)_2NAlCl_3^-$.

Preferred anions $Y^-$ are selected from $AlBrCl_3^-$, $Al_2Cl_7^-$, $Al_2BrCl_6^-$, $Al_3Cl_{10}^-$, $Al_3BrCl_9^-$.

The anions $Y^-$ are more preferably selected from $Al_2Cl_7^-$, $Al_3Cl_{10}^-$, and are especially $Al_2Cl_7^-$.

Such an ionic liquid is prepared especially by adding the appropriate amount of aluminum chloride to the ionic liquid or to an ammonium chloride.

In the superacidic ionic liquid comprising an organic cation and an inorganic anion, where the anion is a superacidic aluminum trichloride-Lewis base adduct, the molar ratio of aluminum trichloride to Lewis base is preferably $>1.0$, particularly $\geq 1.5$, more particularly $\geq 2.0$. The molar ratio of aluminum trichloride to Lewis base is preferably $\leq 3.0$, particularly $\leq 2.5$, most preferably $=2.0$.

For the superacidic ionic liquid used in accordance with the invention, the Hammett function $H_0$ is preferably in the range from −16 to −20, particularly in the range from −17 to −19.

EXAMPLES

General Experimental Procedure:

In each case, a 250 ml Miniplant stirred vessel with disc stirrer, internal thermometer, jacketed coil condenser, 200 ml feed vessel with Teflon tap (10 mm bore), thermometer and pressure equalizer to the jacketed coil condenser, stirrer driver with speed display, sampling attachment with tap and septum, and inertization with argon dried over sodium hydroxide, was used.

The ionic liquid (IL) (150 ml) was initially charged in the stirred vessel under argon, and the methylcyclopentane-containing organic mixture to be isomerized (30 ml) was introduced into the feed vessel. The particular amount specified of a copper(II) salt was added to the ionic liquid. After heating all reactants to 60° C., the entire contents of the feed vessel were transferred by opening the Teflon tap within 1-2 seconds into the stirred vessel containing the IL while stirring. At defined time intervals, 5 ml of sample were taken each time by means of a 30 cm cannula and syringe through the sampling stub with septum. After approx. 2 minutes, the lighter organic phase which had separated out was introduced from the syringe into approx. 5 ml of 10% by weight aqueous sodium-EDTA solution and shaken. The phases were then separated. The organic phase was diluted with 2 ml of methylene chloride and, after drying with anhydrous sodium sulfate, analyzed by means of GC.

The examples which follow relate to the isomerization of methylcyclopentane to cyclohexane.

Abbreviations Used:
RE: reaction equilibrium
MCP: methylcyclopentane

CH: cyclohexane
TMA: trimethylammonium
TEA: triethylammonium
EMIM: 1-ethyl-3-methylimidazolium

Example 1 (Comparative)

IL: TMA-Al$_2$Cl$_7$
Additive: none
Organic phase: pure MCP
Time until attainment of RE (80% MCP conversion): 180 min

Example 2

IL: TMA-Al$_2$Cl$_7$
Additive: 1.22 g of CuCl$_2$
Organic phase: pure MCP
Time until attainment of RE (80% MCP conversion): 15 min

Example 3 (Comparative)

IL: TMA-Al$_2$Cl$_7$
Additive: none
Organic phase: 39% by weight of MCP, 12% by weight of CH, 49% by weight of n-hexane
Time until attainment of RE (77% MCP conversion): 120 min

Example 4

IL: TMA-Al$_2$Cl$_7$
Additive: 0.1 g of CuCl$_2$
Organic phase: 39% by weight of MCP, 12% by weight of CH, 49% by weight of n-hexane
Time until attainment of RE (77% MCP conversion): 70 min

Example 5

IL: TMA-Al$_2$Cl$_7$
Additive: 0.5 g of CuCl$_2$
Organic phase: 39% by weight of MCP, 12% by weight of CH, 49% by weight of n-hexane
Time until attainment of RE (77% MCP conversion): 30 min

Example 6

IL: TMA-Al$_2$Cl$_7$
Additive: 1.0 g of CuCl$_2$
Organic phase: 39% by weight of MCP, 12% by weight of CH, 49% by weight of n-hexane
Time until attainment of RE (77% MCP conversion): 3 min

Example 7

IL: TMA-Al$_2$Cl$_7$
Additive: 0.1 g of CuO
Organic phase: 39% by weight of MCP, 12% by weight of CH, 49% by weight of n-hexane
Time until attainment of RE (77% MCP conversion): 70 min

Example 8

IL: TMA-Al$_2$Cl$_7$
Additive: 0.5 g of CuO
Organic phase: 39% by weight of MCP, 12% by weight of CH, 49% by weight of n-hexane
Time until attainment of RE (77% MCP conversion): 30 min

Example 9

IL: TMA-Al$_2$Cl$_7$
Additive: 1.0 g of CuO
Organic phase: 39% by weight of MCP, 12% by weight of CH, 49% by weight of n-hexane
Time until attainment of RE (77% MCP conversion): 3 min

Example 10 (Comparative)

IL: TEA-Al$_2$C$_{17}$
Additive: none
Organic phase: 39% by weight of MCP, 12% by weight of CH, 49% by weight of n-hexane
Time until attainment of RE (77% MCP conversion): 60 min

Example 11

IL: TEA-Al$_2$Cl$_7$
Additive: 0.3 g of CuO
Organic phase: 39% by weight of MCP, 12% by weight of CH, 49% by weight of n-hexane
Time until attainment of RE (77% MCP conversion): 20 min

Example 12

IL: TEA-Al$_2$Cl$_7$
Additive: 1.22 g of CuCl$_2$
Organic phase: 39% by weight of MCP, 12% by weight of CH, 49% by weight of n-hexane
Time until attainment of RE (77% MCP conversion): 10 min

Example 13 (Comparative)

IL: EMIM-Al$_2$Cl$_7$
Additive: none
Organic phase: 39% by weight of MCP, 12% by weight of CH, 49% by weight of n-hexane
RE (77% MCP conversion) not attained after 300 min, MCP conversion after 300 min: 70%

Example 14

IL: EMIM-Al$_2$Cl$_7$
Additive: 1.22 g of CuCl$_2$
Organic phase: 39% by weight of MCP, 12% by weight of CH, 49% by weight of n-hexane
Time until attainment of RE (80% MCP conversion): 90 min

Example 15 (Comparative)

IL: pyridinium-Al$_2$Cl$_7$
Additive: none
Organic phase: 39% by weight of MCP, 12% by weight of CH, 49% by weight of n-hexane
Time until attainment of RE (80% MCP conversion): 90 min

Example 16

IL: pyridinium-$Al_2Cl_7$
Additive: 1.22 g of $CuCl_2$
Organic phase: 39% by weight of MCP, 12% by weight of CH, 49% by weight of n-hexane
Time until attainment of RE (80% MCP conversion): 10 min

Example 17 (Comparative)

IL: n-butylpyridinium-$Al_2Cl_7$
Additive: none
Organic phase: 39% by weight of MCP, 12% by weight of CH, 49% by weight of n-hexane
RE (77% MCP conversion) not attained after 300 min, MCP conversion after 300 min: 67%

Example 18

IL: n-butylpyridinium-$Al_2Cl_7$
Additive: 1.22 g of $CuCl_2$
Organic phase: 39% by weight of MCP, 12% by weight of CH, 49% by weight of n-hexane
Time until attainment of RE (80% MCP conversion): 60 min

The invention claimed is:

1. A process for isomerizing a saturated, branched and cyclic hydrocarbon, in which a tertiary carbon atom of the hydrocarbon is converted to a secondary carbon atom in the course of isomerization, which comprises performing the isomerization in the presence of a superacidic ionic liquid comprising an organic cation and an inorganic anion, where the anion is a superacidic aluminum trichloride-Lewis base adduct, and 0.1 to 1.5% by weight of a copper(II) compound, based on the ionic liquid used.

2. The process according to claim 1, wherein the molar ratio of aluminum trichloride to Lewis base is >1.0 to ≦3.0.

3. The process according to claim 1, wherein the molar ratio of aluminum trichloride to Lewis base is ≧2.0 to ≦2.5.

4. The process according to claim 1, wherein the copper(II) compound is a copper(II) salt.

5. The process according to claim 1, wherein the copper(II) compound is $CuCl_2$, CuO, $CuSO_4$, $CuBr_2$ or $CuI_2$.

6. The process according to claim 1, wherein the isomerization is performed in the presence of 0.5 to 1.5% by weight of the copper(II) compound, based on the ionic liquid used.

7. The process according to claim 1, wherein the hydrocarbon to be isomerized is a $C_{4-18}$ hydrocarbon.

8. The process according to claim 1, wherein the hydrocarbon to be isomerized is a $C_{5-8}$ hydrocarbon.

9. The process according claim 1, for isomerizing methylcyclopentane to cyclohexane.

10. The process according to claim 1, for isomerizing 1,2-dimethylcyclopentane, 1,3-dimethylcyclopentane or 1,1-dimethylcyclopentane to methylcyclohexane.

11. The process according to claim 1, wherein the Hammett function $H_0$ for the superacidic ionic liquid comprising aluminum chloride is in the range from −16 to −20.

12. The process according to claim 1, wherein the organic cation is an ammonium ion, optionally $C_{1-4}$-alkyl-substituted pyridinium ion or optionally $C_{1-4}$-alkyl-substituted imidazolium ion.

13. The process according to claim 1, wherein the organic cation is a trimethylammonium ion, triethylammonium ion, unsubstituted pyridinium ion or 1-ethyl-3-methylimidazolium ion.

14. The process according to claim 1, wherein the inorganic anion is $Al_2Cl_7^-$ or $Al_2Cl_6Br^-$.

15. The process according to claim 1, wherein the isomerization is performed at a temperature in the range from −20 to 150° C.

16. The process according to claim 1, wherein the isomerization is performed at an absolute pressure in the range from 1 to 10 bar.

17. The process according to claim 1, wherein the hydrocarbon to be isomerized is used in a concentration in the range from 1 to 90% by weight, based on the ionic liquid.

* * * * *